United States Patent [19]

Takeda

[11] 4,143,657
[45] Mar. 13, 1979

[54] EARPLUG

[76] Inventor: Hidetaka Takeda, 4,18, Shirogane 1-chome,, Chuo-ku, Fukuoka-shi, Fukuoka, Japan

[21] Appl. No.: 798,503

[22] Filed: May 19, 1977

[51] Int. Cl.² ............................................. A61F 11/02
[52] U.S. Cl. ..................................................... 128/152
[58] Field of Search ................................. 128/152, 151

[56] References Cited

U.S. PATENT DOCUMENTS 3,440,314   4/1969   Frisch .............................. 128/151 X

FOREIGN PATENT DOCUMENTS 66949   1/1892   Fed. Rep. of Germany ........... 128/152
925889  5/1963   United Kingdom ..................... 128/152

Primary Examiner—Henry J. Recla
Attorney, Agent, or Firm—Frank J. Jordan

[57] ABSTRACT

A cocoon-shaped earplug is provided with a non-linear longitudinal hole.

Since the hole is not staight the "excessive" sound which would normally injure the labyrinth of the ear can be substantially prevented from entering the ear.

8 Claims, 4 Drawing Figures

EARPLUG

BACKGROUND OF THE INVENTION

This invention relates to an earplug which can effectively reduce the amount of noise entering into the ears.

At the present time when the standard noise level at 2000 cps is generally considered to be approximately 70 to 80 phons, an earplug which has a noise interruption rate ranging from 40 to 50 phons will be sufficient to protect the labyrinth of the ear from "excessive sound" which may be of 110 to 120 phons.

A conventional earplug is constructed such that a straight elongated hole passes through the earplug body and the diameter of the hole is substantially large and furthermore, the earplug body is usually made of a plastic material.

Accordingly, the conventional plug suffers from the following disadvantages:

(i) The maximum noise interruption rate obtained by the above earplug is 40 db when the noise level exceeds 2000 cps.

This is explicitly shown in FIG. 4 which is a performance graph wherein the frequency of the sound is the abscissa and the noise interruption rate is on the ordinate.

(ii) Since the material of the earplug is plastic, a person who wears the earplugs feels uncomfortable and becomes fatigued with their extended use.

SUMMARY OF THE INVENTION

It is an object of the present invention to provide an earplug which will resolve the aforementioned problems and which can efficiently interrupt noise which is harmful for the human body.

It is another object of the the invention to provide an earplug which is so constructed as to be particularly useful in the reduction of high frequency sound.

Other objects and advantages of the invention will become readily apparent to persons versed in the art from the following description of the invention.

According to the present invention there is provided a plug body of a relatively flexible material and having a longitudinally extending, non-linear hole therethrough.

DETAILED DESCRIPTION OF THE INVENTION

The construction of the earplug of this invention is hereinafter explained in relation to the attached drawings.

Figure 1:
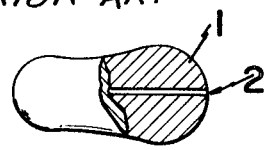
FIG. 1 is a side view partially broken away of a conventional earplug.
Figure 2:
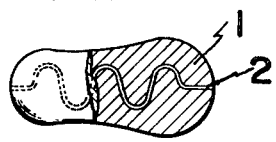
FIG. 2 is a side view partially broken away of a cocoon-shaped earplug of this invention which is provided with a zigzag longitudinal hole therethrough.
Figure 3:
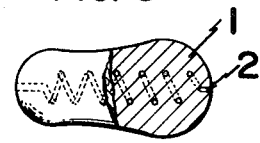
FIG. 3 is a side view partially broken away of a cocoon-shaped earplug of this invention which is provided with a spiral longitudinal hole therethrough.

Referring to FIGS. 2 and 3 it will be seen that, a plug body 1 is provided preferably shaped like a cocoon and made of an elastic soft material such as silicon rubber.

A non-linear, elongated hole 2 extends through the plug body 1 longitudinally. This non-liner hole 2 may take any one of a variety of shapes. The presently preferred constructions are shown in FIG. 2 and FIG. 3. FIG. 2 shows a zigzag-shaped hole of an undulating or sinuous configuration while FIG. 3 shows a spirally-shaped hole. The selection of the shape or the diameter of the hole may be determined on the basis of the noise interruption rate to be achieved.

In actual use a pair of earplugs are employed, and the two earplugs are preferably connected by a string or the like to prevent the loss of the plugs.

The manner in which the earplug of this invention works is hereinafter disclosed.

In general, the intensity of sound is shown by the following formula.

$$I = \tfrac{1}{2} f c w^2 a^2$$

wherein
- f = the density of the medium which transfers the sound
- c = sound velocity
- w = frequency
- a = amplitude This formula shows that the shorter the wave length, the stronger the intensity of sound becomes so that the labyrinth structure of the ear becomes more susceptible to degeneration.

Furthermore, the shorter the wave length, the greater is the tendency for the sound to travel in a straight uninterupted path. Accordingly, such a wave is prevented or at least greatly inhibited from passing through the hole if it is shaped in non-linear manner.

The earplug of this invention specifically absorbs (interrupts) short-wave high amplitude sound since the hole within the earplug is shaped in a non-linear manner.

Figure 4:
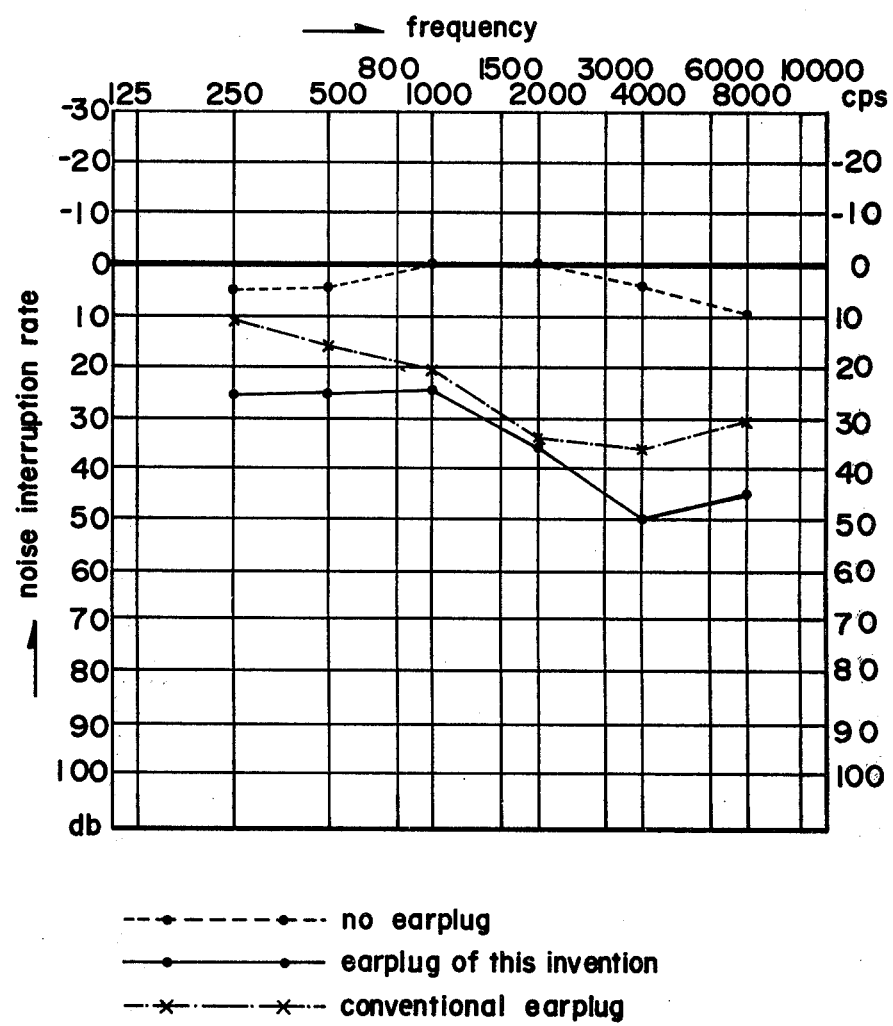
FIG. 4 is a graph comparing the noise interruption rate of the earplug of this invention with that of a conventional earplug.

FIG. 4 shows the above phenomenon clearly wherein the noise-interruption rate of the earplug of this invention and that of a conventional-type earplug are compared with each other.

According to this invention, since the earplug has a non-linear elongated hole, sound which has a long wave-length such as is characteristic of speaking tones passes through the hole without being completely absorbed by the earplug, while sound or noise which is harmful to the labyrinth of the ear can be effectively absorbed. Furthermore, since the earplug body is made of an elastic material such as silicon rubber, the user can wear the earplugs of the invention without incurring discomfort (or fatigue).

What we claim is:

1. An earplug comprising a plug body formed of a relatively flexible material to fit within the auditory canal and having a longitudinally extending zigzag shaped passage therethrough extending from a sound inlet to a sound outlet, said zigzag-shaped passage having the same diameter throughout said plug body from the sound inlet to the sound outlet, said zigzag-shaped passage including more than two turns.

2. An earplug according to claim 1, wherein said plug body comprises:
   a first semi-spherical portion having said sound inlet,
   a second semi-spherical portion having said sound outlet, and
   an intermediate neck portion which connects said two semi-spherical portions.

3. An earplug according to claim 2, wherein one of said semi-spherical protions has a diameter greater than the other semi-spherical portion.

4. An earplug according to claim 2, wherein said zigzag-shaped passage has an undulating configuration.

5. An earplug according to claim 2, wherein said zigzag-shaped passage has a sinuous configuration.

6. An earplug comprising a plug body formed on a relatively flexible material to fit within the auditory canal and having a longitudinally extending spiral-shaped passage therethrough extending from a sound inlet to a sound outlet, said spiral-shaped passage having the same diameter throughout said plug body from the sound inlet to the sound outlet.

7. An earplug according to claim 6, wherein said plug body comprises:
 a first semi-spherical portion having said sound inlet,
 a second semi-spherical portion having said sound outlet, and
 an intermediate neck portion which connects said two semi-spherical portions.

8. An earplug according to claim 6, wherein one of said semi-spherical portions has a diameter greater than the other semi-spherical portion.

* * * * *